United States Patent [19]

Hargrave et al.

[11] Patent Number: 4,618,677
[45] Date of Patent: Oct. 21, 1986

[54] SUBSTITUTED PHENYLALKYL-(PIPERAZINYL OR HOMOPIPERAZINYL)ALKYL-THIOLS AND -THIOCARBAMATES USEFUL FOR THE TREATMENT OF IMMUNOLOGICAL, INFLAMMATORY, AND ALLERGIC DISORDERS

[75] Inventors: Karl D. Hargrave, Brookfield Center; John P. Devlin, Sharon; Edward A. Barsumian, Danbury, all of Conn.

[73] Assignee: Boehringer Ingelheim Limited, Ridgefield, Conn.

[21] Appl. No.: 668,089

[22] Filed: Nov. 5, 1984

Related U.S. Application Data

[63] Continuation-in-part of Ser. No. 499,188, May 31, 1984, abandoned.

[51] Int. Cl.<sup>4</sup> ............... C07D 241/38; A61K 31/495
[52] U.S. Cl. .................................. 544/400; 540/575; 514/218; 514/255
[58] Field of Search ...................... 544/400; 514/255

[56] References Cited

FOREIGN PATENT DOCUMENTS 2551355  5/1976  Fed. Rep. of Germany .
1286198  1/1962  France .
  13468  6/1968  Japan .
 952142  3/1964  United Kingdom .

OTHER PUBLICATIONS

Baltzly et al, J.A.C.S. 66; 263 (1944).
Soc. pour l'ind. Chim., a Bale, Chem. Abst., vol. 32, 1942; eq. French 815575.

Primary Examiner—Donald G. Daus
Assistant Examiner—Cecilia Shen
Attorney, Agent, or Firm—David E. Frankhouser; Alan R. Stempel; Charles J. Herron

[57] ABSTRACT

Compounds of the formula

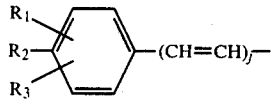

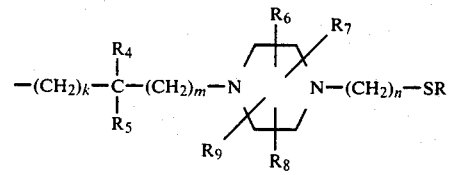

wherein
R is hydrogen or

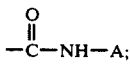

A is alkyl of 1 to 8 carbon atoms; cycloalkyl of 3 to 7 carbon atoms; phenyl; or phenyl mono-, di- or tri-substituted independently with alkyl of 1 to 4 carbon atoms, halogen, trihalomethyl, alkoxy of 1 to 3 carbon atoms, carboxylic acyl of 1 to 3 carbon atoms, carboxyl, (alkoxy of 1 to 3 carbon atoms)carbonyl, nitro, cyano or di(alkyl of 1 to 3 carbon atoms)amino;
$R_1$, $R_2$ and $R_3$, are independently hydrogen, halogen, alkyl of 1 to 4 carbon atoms, trihalomethyl, nitro, cyano, di(alkyl of 1 to 4 carbon atoms)amino, (alkoxy of 1 to 4 carbon atoms)carbonyl, alkoxy of 1 to 4 carbon atoms or hydroxyl;
$R_4$ and $R_5$ are independently hydrogen, alkyl of 1 to 4 carbon atoms, or phenyl;
$R_6$, $R_7$, $R_8$ and $R_9$ are independently hydrogen or methyl;
Y is —CH$_2$— or —CH$_2$—CH$_2$—;
j is 0 or 1;
k and m are independently 0, 1, 2, or 3, their sum being no more than 6 and must be 0 when j is 1;
n is 2, 3, or 4, with the proviso that n must be 3 or 4 when $R_1$ is hydrogen or 2-methyl, $R_2$, $R_3$, $R_4$, $R_5$, $R_6$, $R_7$, $R_8$, $R_9$ and R are each hydrogen and j, k, and m are each 0, and Y is —CH$_2$—; and non-toxic, pharmaceutically acceptable acid addition salts thereof are useful for the treatment of immunological, inflammatory and allergic disorders.

27 Claims, No Drawings

SUBSTITUTED PHENYLALKYL-(PIPERAZINYL OR HOMOPIPERAZINYL)ALKYL-THIOLS AND -THIOCARBAMATES USEFUL FOR THE TREATMENT OF IMMUNOLOGICAL, INFLAMMATORY, AND ALLERGIC DISORDERS

This application is a continuation-in-part of application Ser. No. 6/499,188, filed May 31, 1984, now abandoned.

This invention relates to novel substituted phenylalkyl(piperazinyl or homopiperazinyl)alkyl-thiols and -thiocarbamates and non-toxic acid addition salts thereof, to a method of preparing these compounds, to pharmaceutical compositions containing them as active ingredients, and to therapeutic methods of using them. By virtue of their inhibition of mediator release in cell systems, the compounds are useful for the treatment of allergic disorders.

More particularly, the present invention relates to novel substituted phenylalkyl(piperazinyl or homopiperazinyl)alkyl-thiols or -thiocarbamates represented by the formula

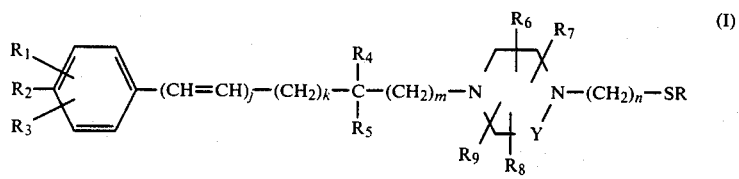

wherein
R is hydrogen or

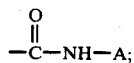

A is alkyl of 1 to 8 carbon atoms, cycloalkyl of 3 to 7 carbon atoms, phenyl or phenyl mono-, di-, or tri-substituted independently with alkyl of 1 to 4 carbon atoms, halogen, trihalomethyl, alkoxy of 1 to 3 carbon atoms, carboxylic acyl of 1 to 3 carbon atoms, carboxyl, (alkoxy of 1 to 3 carbon atoms)carbonyl, nitro, cyano or di(alkyl of 1 to 3 carbon atoms)amino;
$R_1$, $R_2$ and $R_3$, are independently hydrogen, halogen, alkyl of 1 to 4 carbon atoms, trihalomethyl, nitro, cyano, di(alkyl of 1 to 4 carbon atoms)amino, (alkoxy of 1 to 4 carbon atoms)carbonyl, alkoxy of 1 to 4 carbon atoms or hydroxyl;

$R_4$ and $R_5$ are independently hydrogen, alkyl of 1 to 4 carbon atoms, or phenyl;
$R_6$, $R_7$, $R_8$ and $R_9$ are independently hydrogen or methyl;
Y is $-CH_2-$ or $-CH_2-CH_2-$;
j is 0 or 1;
k and m are independently 0, 1, 2, or 3, their sum being no more than 6 and must be 0 when j is 1;
n is 2, 3, or 4, with the proviso that n must be 3 or 4 when $R_1$ is hydrogen or 2-methyl, $R_2$, $R_3$, $R_4$, $R_5$, $R_6$, $R_7$, $R_8$, $R_9$ and R are each hydrogen, and j, k, and m are each 0, and Y is $-CH_2-$;
or a non-toxic, pharmaceutically acceptable acid addition salt thereof.

Specific examples of variables A, $R_1$, $R_2$, $R_3$, $R_4$, and $R_5$ are the following:

A—Methyl, ethyl, propyl, butyl, pentyl, hexyl, heptyl, octyl or possible isomers thereof; cyclopropyl, cyclobutyl, cyclopentyl, cyclohexyl or cycloheptyl. The optional substituents on the phenyl group: methyl, ethyl, propyl, butyl or possible isomers thereof; fluorine, chlorine or bromine; trifluoromethyl or trichloromethyl; methoxy, ethoxy, propoxy, butoxy or possible isomers thereof; acetyl, propionyl or butyryl; methoxycarbonyl, ethoxycarbonyl or propoxycarbonyl; dimethylamino, N-methylethylamino, diethylamino, N-ethyl-propylamino, N-methyl-propylamino or dipropylamino.

$R_1$, $R_2$ and $R_3$-Fluorine, chlorine or bromine; methyl, ethyl, propyl, butyl or a possible isomer thereof; trifluoromethyl or trichloromethyl; dimethylamino, N-methyl-ethylamino, diethylamino, N-ethyl-propylamino, N-methyl-propylamino or dipropylamino; methoxycarbonyl, ethoxycarbonyl or propoxycarbonyl; methoxy, ethoxy, propoxy, butoxy or possible isomers thereof.

$R_4$ and $R_5$-Methyl, ethyl, propyl or isopropyl.

It will be appreciated by those skilled in the art that, when Y in formula I is $-CH_2-$, the compounds of formula I are the piperazines of the formula

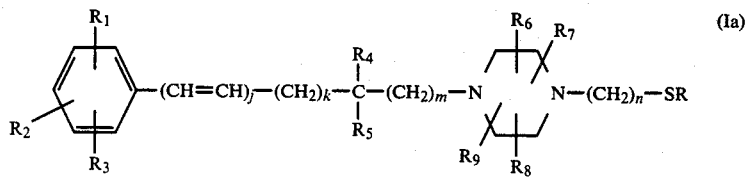

and, when Y in formula I is $-CH_2CH_2-$, the compounds of formula I are the homopiperazines of the formula

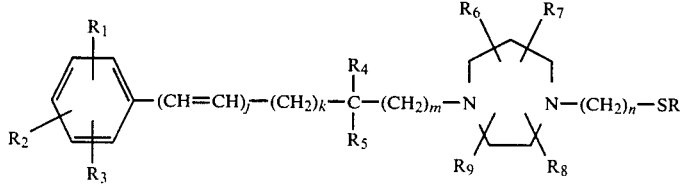

wherein $R_1$, $R_2$, $R_3$, $R_4$, $R_5$, $R_6$, $R_7$, $R_8$, j, k, m, n, and R have the meanings as defined above with respect to formula I. The piperazines of formula Ia are preferred.

In subgeneric aspects, the invention comprehends the following classes of compounds, or a non-toxic, pharmaceutically acceptable acid addition salt thereof:

A. A compound of the formula

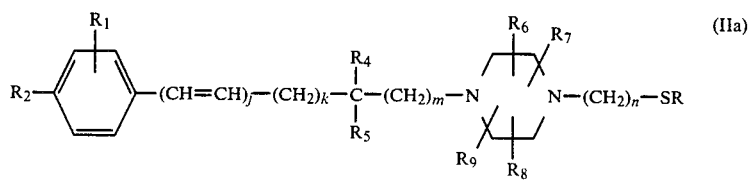

or

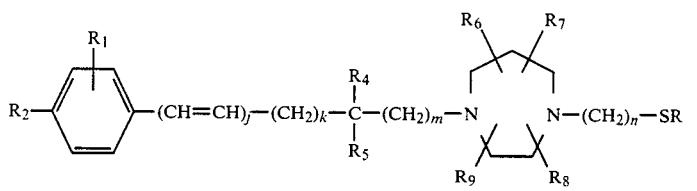

wherein R, $R_1$, $R_2$, $R_4$, $R_5$, $R_6$, $R_7$, $R_8$, j, k, m, and n have the meanings defined above with respect to formula I.

B. A compound of the formula

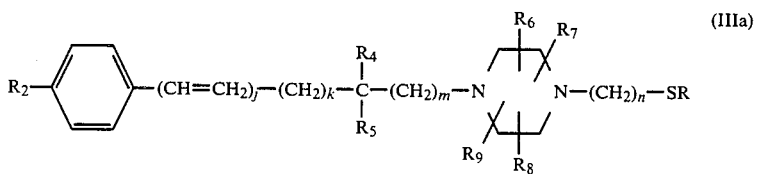

or

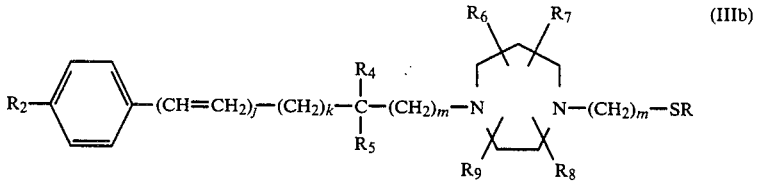

wherein R, $R_2$, $R_4$, $R_5$, $R_6$, $R_7$, $R_8$, $R_9$, j, k, m, and n have the meanings defined above with respect to formula I.

C. A compound of the formula

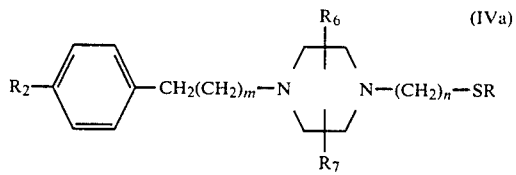

or (IVb)

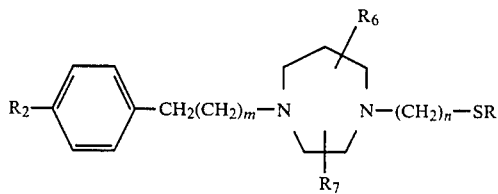

wherein R, $R_2$, $R_6$, $R_7$, m, and n have the meanings defined above with respect to formula I.

D. A compound of the formula

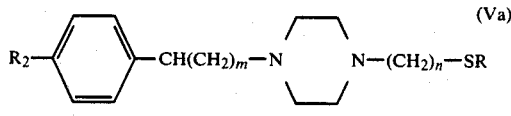

(Va)

or

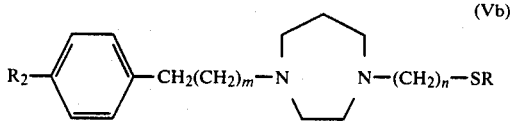

(Vb)

wherein R, $R_2$, m, and n have the meanings defined above with respect to formula I.

The preferred compounds of the invention are those wherein $R_1$ is a group other than hydrogen fixed in the 4-position of the phenyl ring. The most preferred compounds are those wherein $R_1$ is chlorine fixed in the 4-position of the phenyl ring. The compounds wherein $R_1$ is chlorine fixed in the 4-position or wherein $R_2$ and $R_3$ are each hydrogen are particularly preferred. A particularly preferred subgenus of compounds is represented by formula VIa and VIb below:

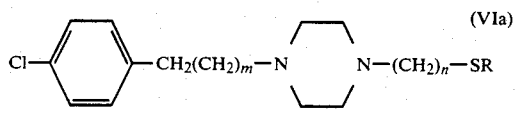

(VIa)

or

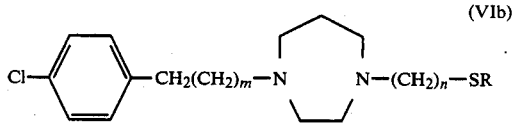

(VIb)

wherein R, m, and n have the meanings defined above with respect to formula I.

The compounds of formula VIa or VIb wherein m is 0 or 1 or n is 2 or 3 are preferred. The compounds wherein m is 0 and n is 2 or 3 are most preferred.

The compounds depicted above are either thiols, when R is hydrogen, or thiocarbamates when S is a group represented by —CONHA. The thiols (R=H) are most preferred. When R is —CONHA, the preferred groups represented by A are alkyl and cycloalkyl.

The compounds of formula I are capable of inhibiting in vitro the IgE-mediated release of histamine from human peripheral blood leukocytes (basophils), from guinea pig basophils, and from rat peritoneal mast cells, and are useful in warm-blooded animals for inhibiting the antigen-induced cellular release of histamine and/or other mediators of the allergic reaction. The compounds of formula I can be used for the treatment of allergic disorders, such as allergic asthma, allergic rhinitis, allergic conjunctivitis, hay fever, urticaria, food allergies, and the like.

By virtue of their ability to inhibit cellular mediator release, the compounds may also be useful for the treatment of inflammatory or immunological disorder.

For pharmaceutical purposes as antiallergic agents, the compounds of the present invention are administered topically to the skin or preferably to the mucosa of the eye, nose, or respiratory tract in conventional pharmaceutical compositions, that is compositions comprising an inert pharmaceutical carrier and an effective amount of the active ingredient.

For administration to the respiratory tract, the compounds can be administered as an aerosol or solution for a nebulizer, or as a microfine powder for insufflation alone or in combination with an inert carrier such as lactose. In such a case the particles of active compounds suitably have diameters of less than 20 microns, preferably less than 10 microns. Where appropriate, small amounts of other antiallergic and antiasthmatic bronchodilators, for example sympathomimetic amines such as isoprenaline, isoetharine, metaproterenol, salbutamol, phenylephrine, fenoterol and ephedrine; xanthine derivatives such as theophylline and aminophylline; and corticosteroids such as prednisolone and adrenal stimulants such as ACTH may be included.

For administration to the skin, the compounds can be administered as an ointment, cream, lotion, gel, or aerosol. Solutions for topical application to the nose can conveniently be administered by nasal sprays or drops. In addition, a sterile ointment can be formulated for application to the eye.

Topical solutions for the nose and the eye may contain, in addition to the compounds of this invention, suitable buffers, tonicity adjusters, microbial preservatives, antioxidants and viscosity-increasing agents in an aqueous vehicle. Examples of agents used to increase viscosity are polyvinyl alcohol cellulose derivatives, polyvinylpyrrolidone, polysorbates or glycerin. Microbial preservatives added may include benzalkonium chloride, thimerosal, chlorobutanol or phenylethyl alcohol. Topical preparations for the eye may also be prepared as ointments in a suitable inert base consisting of mineral oil, petrolatum, polyethylene glycols or lanolin derivatives along with microbial preservatives.

Solutions for the topical administration of the compounds of formula I to the eye or nasal mucosa can preferably contain 0.005% (w/w) to about 1% of the active ingredient, depending upon the solubility of the particular compound and the desired pH of the solution.

Ointments for topical administration to the skin can preferably contain about 0.1% to about 5% (w/w) of the active ingredient.

The topical formulations containing the active ingredients can be administered as needed depending upon the nature and severity of the allergic disorder being treated. In general, the formulations can be applied topically one to four times per day.

Certain compounds of formula I inhibit in vitro the histamine-induced contraction of isolated guinea pig ileum and are useful in warm-blooded animals for antagonizing the action of histamine at the histamine ($H_1$) receptor. Accordingly, these compounds can be employed in a conventional manner as antihistamine agents for the treatment of allergic disorders, for example allergic rhinitis, vasomotor rhinitis, allergic conjunctivitis, hay fever, urticaria, and food allergies. Compounds showing antihistamine activity are shown in Table 2 of Example 49.

The compounds embraced by formula I may be prepared by reacting a phenylalkyl-piperazine or -homopiperazine of the formula

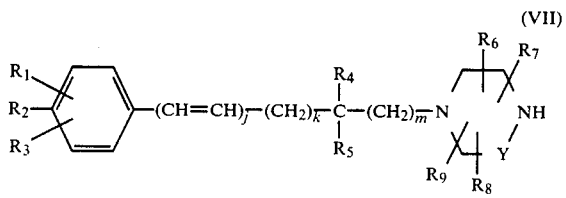

wherein $R_1$, $R_2$, $R_3$, $R_4$, $R_5$, $R_6$, $R_7$, $R_8$, $R_9$, j, k, m and Y have the meanings previously defined, with an alkyl halide of the formula $$X-(CH_2)_n-Z \qquad (VIII)$$

wherein
X and Z are indentical or different halogens, and
n has the meanings previously defined,
to provide the alkyl halide of the formula

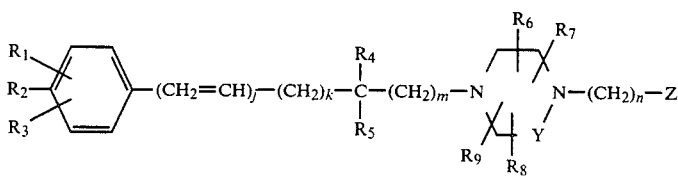

wherein $R_1$, $R_2$, $R_3$, $R_4$, $R_5$, $R_6$, $R_7$, $R_8$, $R_9$, Y, Z, j, k, m and n have the meanings previously defined; the alkyl halide IV on reaction with thiourea, followed by hydrolysis of the intermediate isothiouronium halide can provide an end product of the formula I wherein R is hydrogen, and, if desired, reacting said end product with an isocyanate of the formula $$A-N=C=O \qquad (X)$$

wherein A has the meanings previously defined, to obtain an end product of the formula I wherein R is —CO—NH—A.

The alkylation reaction described may be performed in a suitable solvent, such as water, dimethyl sulfoxide, dimethyl formamide, a lower alkanol of up to five carbon atoms, tetrahydrofuran or acetone, in the presence of a strong inorganic or organic base such as sodium or potassium hydroxide, a trialkylamine or pyridine and at room or elevated temperature up to the boiling point of the reaction mixture. The reaction time is temperature-dependent and may be one to several hours.

The subsequent reaction of a phenylalkyl piperazinylalkyl halide of the formula IX with thiourea is carried out in the same solvents and bases as those mentioned in connection with the alkylation process; the reaction temperature may be up to the boiling point of the reaction mixture. Hydrolysis of the intermediate isothiouronium halide may be effected by the addition of water and strong inorganic base, e.g. sodium or potassium hydroxide at room or elevated temperature up to the boiling point of the reaction mixture. With this reaction free thiols of the formula I are obtained.

For the preparation of an end product wherein R is —CO—NH—A, an above-mentioned thiol is reacted with an isocyanate of the formula X in the presence of a suitable inert solvent such as dioxane, tetrahydrofuran, ether, toluene or chlorinated hydrocarbons and optionally in the presence of an inorganic or organic base such as sodium or potassium carbonate, a trialkylamine or pyridine.

The temperature may arise up to a reflux while the reaction time depends on the starting material and temperature used and may last from 30 minutes to several hours.

The compounds embraced by formula I are basic and therefore form addition salts with inorganic or organic acids. Examples of non-toxic, pharmacologically acceptable acid addition salts are those formed with hydrohalic acid, especially hydrochloric or hydrobromic acid, or with nitric acid, sulfuric acid, o-phosphoric acid, citric acid, maleic acid, fumaric acid, propionic acid, butyric acid, acetic acid, succinic acid, methanesulfonic acid, benzenesulfonic acid, p-toluenesulfonic acid, or the like.

The starting compounds are known or may be prepared by known methods.

For example, compounds of the formula VII are described in British Pat. No. 480,358 and J. Am. Chem. Soc. 66, 263 (1944).

Compounds of the formula IX are known, for example, from Helv. Chim. Acta 41, 1072 (1958) and Monatshefte 87, 701 (1956).

The following examples illustrate the present invention and will enable others skilled in the art to understand it more completely. It should be understood, however, that the invention is not limited solely to the particular examples given below

EXAMPLE 1

3-(4-Benzylpiperazin-1-yl)propanethiol dihydrochloride (a) 31.5 g of 1-bromo-3-chloropropane were added to a mixture of 35 g of 1-benzylpiperazine, 150 ml of dimethyl sulfoxide and 25 g of potassium hydroxide. The resulting mixture was stirred at room temperature for 3 hours. Water was added to the resulting solution, the reaction product was extracted with ether, dried (magnesium sulfate), and the salt was precipitated with ethereal hydrochloric acid to give 35.6 g (55% of theory) of 1-benzyl-4-(3-chloropropyl)piperazine dihydrochloride as a white crystalline solid.

(b) 15 g of thiourea were added to a solution of 35 g of 1-benzyl-4-(3-chloropropyl)piperazine dihydrochloride, 20 g of triethylamine and 250 ml of reagent ethanol, and the mixture was refluxed for 8 hours. After the addition of a solution of 10 g of sodium hydroxide in 50 ml of water, the resulting mixture was refluxed for 4 additional hours. The ethanol was removed in vacuo, and water added to the residue which was extracted with methylene chloride, dried (sodium sulfate), and the salt was precipitated with ethereal hydrochloric acid to give 25.1 g (78% of theory) of 3-(4-benzylpiperazin-1-yl)propanethiol dihydrochloride as a white crystalline solid, M.p. 270°–273° C. (dec.).

EXAMPLE 2

N-Phenyl-S-[3-(4-benzylpiperazin-1-yl)propyl]thiocarbamate dihydrochloride monohydrate 1.6 g of phenyl isocyanate were added to a solution of 4.0 g of 3-(4-benzylpiperazin-1-yl)propanethiol dihydrochloride and 2.6 g of triethylamine in 50 ml of methylene chloride. The mixture was refluxed for four hours, washed with water and dried (sodium sulfate). Precipitation of the salt with ethereal hydrochloric acid gave 1.2 g (20% of theory) of N-phenyl-S-[3-(4-benzylpiperazin-1-yl)-propyl]thiocarbamate dihydrochloride monohydrate as a white crystalline solid, M.p. 216°–219° C.

EXAMPLE 3

3-[4-(4-Chlorobenzyl)piperazin-1-yl]propanethiol dihydrochloride (a) Utilizing the procedure described in Example 1(a), 20.0 g of 1-(4-chlorobenzyl)piperazine, 100 ml of dimethyl sulfoxide, 15.0 g of potassium hydroxide and 15.0 of 1-bromo-3-chloropropane yielded 25.1 g (74% of theory) of 1-(4-chlorobenzyl)-4-(3-chloropropyl)piperazine dihydrochloride as a white crystalline solid.

(b) Utilizing the procedure described in Example 1(b), 6.0 g of thiourea, was reacted with 25.2 g of 1-(4-chlorobenzyl-4-(3-chloropropyl)piperazine dihydrochloride and 8.7 g of triethylamine in 200 ml of reagent ethanol. The hydrolysis was effected with 5.0 g of sodium hydroxide in 50 ml of water. Work-up as described above gave 16.6 g (75% of theory) of 3-[4-(4-chlorobenzyl)piperazine-1-yl]propanethiol dihydrochloride as an off-white crystalline solid, M.p. 257°–260° C.

EXAMPLE 4

N-Methyl-S-{3-[4-(4-chlorobenzyl)piperazin-1-yl]propyl}thiocarbamate dihydrochloride The procedure described in Example 2 was followed, using 0.4 g of methyl isocyanate, 2.0 g of 3-[4-(4-chlorobenzyl)piperazin-1-yl]propanethiol dihydrochloride, 0.7 g of triethylamine and 50 ml of methylene chloride, to give 0.75 g (32% of theory) of N-methyl-S-{3-[4-(4-chlorobenzyl)piperazin-1-yl]propyl}thiocarbamate dihydrochloride as a white crystalline solid, M.p. 240°–243° C.

EXAMPLE 5

N-Isopropyl-S-{3-[4-(4-chlorobenzyl)piperazin-1-yl]propyl}thiocarbamate dihydrochloride The procedure described in Example 2 was followed, using 0.5 g of isopropyl isocyanate, 2.0 g of 3-[4-(4-chlorobenzyl)piperazin-1-yl]propanethiol dihydrochloride, 0.7 g of triethylamine and 50 ml of methylene chloride, to give 0.7 g (28% of theory) of N-isopropyl-S-{3-[4-(4-chlorobenzyl)piperazin-1-yl]propyl}thiocarbamate dihydrochloride as a white crystalline solid, M.p. 247°–250° C.

EXAMPLE 6

N-Cyclohexyl-S-{3-[4-(4-chlorobenzyl)piperazin-1-yl]propyl}thiocarbamate dihydrochloride A mixture of 1.0 g of cyclohexyl isocyanate, 2.1 g of 3-[4-(4-chlorobenzyl)piperazin-1-yl]propanethiol and 10 ml of methylene chloride was stirred at room temperature overnight and then concentrated in vacuo. The residue crystallized upon standing. The product was recrystallized from aqueous ethanol, dissolved in ether, and the ethanol solution was dried (magnesium sulfate). The salt was then precipitated with ethereal hydrochloric acid and recrystallized twice from aqueous ethanol to give 1.2 g (30% of theory) of N-cyclohexyl-S-{3-[4-(4-chlorobenzyl)piperazin-1-yl]propyl}thiocarbamate dihydrochloride as a white crystalline solid, M.p. >165° C. (dec.).

EXAMPLE 7

N-Phenyl-S-{3-[4-(4-chlorobenzyl)piperazin-1-yl]propyl}thiocarbamate dihydrochloride The procedure described in Example 2 was followed, using 4.3 g of phenyl isocyanate, 12.7 g of 3-[4-(4-chlorobenzyl)piperazin-1-yl]propanethiol dihydrochloride, 7.3 g of triethylamine and 100 ml of methylene chloride, to give 9.1 g (53% of theory) of N-phenyl-S-{3-[4-(4-chlorobenzyl)piperazin-1-yl]propyl}thiocarbamate dihydrochloride as a white crystalline solid, M.p. >230° C. (dec.).

EXAMPLE 8

N-(4-n-Butylphenyl)-S-{3-[4-(4-chlorobenzyl)piperazin-1-yl]propyl}thiocarbamate dihydrochloride The procedure described in Example 2 was followed, using 1.0 g of 4-n-butylphenyl isocyanate, 2.0 g of 3-[4-(4-chlorobenzyl)piperazin-1-yl]propanethiol dihydrochloride, 0.7 g of triethylamine and 50 ml of methylene chloride, to give 0.85 g (28% of theory) of N-(4-n-butylphenyl)-S-{3-[4-(4-chlorobenzyl)piperazin-1-yl]propyl}thiocarbamate dihydrochloride as a white crystalline solid, M.p. 243°–246° C.

EXAMPLE 9

N-(4-Fluorophenyl)-S-{3-[4-(4-chlorobenzyl)piperazin-1-yl]propyl}thiocarbamate dihydrochloride The procedure described in Example 2 was followed, using 0.8 g of 4-fluorophenyl isocyanate, 2.2 g of 3-[4-(4-chlorobenzyl)piperazin-1-yl]propanethiol dihydrochloride, 0.6 g of triethylamine and 25 ml of methylene chloride, to give 1.41 g (47% of theory) of N-(4-fluorophenyl)-S-{3-[4-(4-chlorobenzyl)piperazin-1-yl]propyl}thiocarbamate dihydrochloride as a white crystalline solid, M.p. 250°–252° C.

EXAMPLE 10

N-(4-Chlorophenyl)-S-{3-[4-(4-chlorobenzyl)piperazin-1-yl]propyl}thiocarbamate dihydrochloride monohydrate The procedure described in Example 2 was followed, using 1.5 g of 4-chlorophenyl isocyanate, 3.5 g of 3-[4-(4-chlorobenzyl)piperazin-1-yl]propanethiol dihydrochloride, 1.2 g of triethylamine and 50 ml of methylene chloride, to give 1.1 g (21% of theory) of N-(4-chlorophenyl)-S-{3-[4-(4-chlorobenzyl)piperazin-1-yl]propyl}thiocarbamate dihydrochloride monohydrate as an off-white crystalline solid, M.p. 243°–245° C.

EXAMPLE 11

N-(3,4-Dichlorophenyl)-S-{3-[4-(4-chlorobenzyl)piperazin-1-yl]propyl}thiocarbamate dihydrochloride The procedure described in Example 2 was followed, using 1.6 g of 3,4-dichlorophenyl isocyanate, 3.0 g of 3-[4-(4-chlorobenzyl)piperazin-1-yl]propanethiol dihydrochloride, 0.9 g of triethylamine and 50 ml of methylene chloride, to give 1.2 g (26% of theory) of N-(3,4- dichlorophenyl)-S-{3-[4-(4-chlorobenzyl)piperazin-1-yl]propyl}thiocarbamate dihydrochloride as a white crystalline solid, M.p. 227°–230° C.

EXAMPLE 12

N-(2-Methoxyphenyl)-S-{3-[4-(4-chlorobenzyl)piperazin-1-yl]propyl}thiocarbamate dihydrochloride sesquihydrate The procedure described in Example 2 was followed, using 1.3 g of 2-methoxyphenyl isocyanate, 3.0 g of 3-[4-(4-chlorobenzyl)piperazin-1-yl]propanethiol dihydrochloride, 0.9 g of triethylamine and 50 ml of methylene chloride, to give 0.9 g (20% of theory) of N-(2-methoxyphenyl)-S-{3-[4-(chlorobenzyl)piperazin-1-yl]propyl}thiocarbamate dihydrochloride sesquihydrate as an off-white crystalline solid, M.p. 238°–240° C.

EXAMPLE 13

N-(3-Methoxyphenyl)-S-{3-[4-(4-chlorobenzyl)piperazin-1-yl]propyl}thiocarbamate dihydrochloride The procedure described in Example 2 was followed, using 1.3 g of 3-methoxyphenyl isocyanate, 3.0 g of 3-[4-(4-chlorobenzyl)piperazin-1-yl]propanethiol dihydrochloride, 0.9 g of triethylamine and 50 ml of methylene chloride, to give 1.35 g (32% of theory) of N-(3-methoxyphenyl)-S-{3-[4-(4-chlorobenzyl)piperazin-1-yl]propyl}thiocarbamate dihydrochloride as an off-white crystalline solid, M.p. 238°–240° C.

EXAMPLE 14

N-(4-Methoxyphenyl)-S-{3-[4-(4-chlorobenzyl)piperazin-1-yl]propyl}thiocarbamate dihydrochloride monohydrate The procedure described in Example 2 was followed, using 0.9 g of 4-methoxyphenyl isocyanate, 2.0 g of 3-[4-(4-chlorobenzyl)piperazin-1-yl]propanethiol dihydrochloride, 0.7 g of triethylamine and 50 ml of methylene chloride, to give 0.72 g (25% of theory) of N-(4-methoxyphenyl)-S-{3-[4-(4-chlorobenzyl)piperazin-1-yl]propyl}thiocarbamate dihydrochloride monohydrate as an off-white crystalline solid, M.p. 235°–237° C.

EXAMPLE 15

N-(4-Acetylphenyl)-S-{3-[4-(4-chlorobenzyl)piperazin-1-yl]propyl}thiocarbamate dihydrochloride monohydrate The procedure described in Example 2 was followed, using 1.0 g of 4-acetylphenyl isocyanate, 2.0 g of 3-[4-(4-chlorobenzyl)piperazin-1-yl]propanethiol dihydrochloride, 0.7 g of triethylamine and 50 ml of methylene chloride, to give 0.83 g (29% of theory) of N-(4-acetylphenyl)-S-{3-[4-(4-chlorobenzyl)piperazin-1-yl]propyl}thiocarbamate dihydrochloride monohydrate as a white crystalline solid, M.p. 235°–237° C.

EXAMPLE 16

N-(4-Ethoxycarbonylphenyl)-S-{3-[4-(4-chlorobenzyl)-piperazin-1-yl]propyl}thiocarbamate dihydrochloride The procedure described in Example 2 was followed, using 1.1 g of 4-ethoxycarbonylphenyl isocyanate, 2.0 g of 3-[4-(4-chlorobenzyl)piperazin-1-yl]propanethiol dihydrochloride, 0.7 g of triethylamine and 50 ml of methylene chloride, to give 0.85 g (28% of theory) of N-(4-ethoxycarbonylphenyl)-S-{3-[4-(4-chlorobenzyl)piperazin-1-yl]propyl}thiocarbamate dihydrochloride as a white crystalline solid, M.p. 231°–233° C.

EXAMPLE 17

3-[4-(4-Methylbenzyl)piperazin-1-yl]propanethiol dihydrochloride (a) A mixture of 14.0 g of 1-(4-methylbenzyl)piperazine, 8.0 g of potassium hydroxide and 125 ml of dimethyl sulfoxide was stirred for 45 minutes. 11.8 g of 1-bromo-3-chloropropane were then added, and the mixture was stirred for an additional hour. Water was added, and the product was extracted with ether, and the extract was dried (sodium sulfate) and treated with ethereal hydrochloric acid to give 23.3 g (94% of theory) of 1-(4-methylbenzyl)-4-(3-chloropropyl)piperazine dihydrochloride as a white crystalline solid. (b) The procedure described in Example 1(b) was followed, using 7.7 g of thiourea, 23.0 g of 1-(4-methylbenzyl)-4-(3-chloropropyl)piperazine dihydrochloride, 6.5 g of triethylamine and 250 ml of reagent ethanol. The hydrolysis was effected with 6.0 g of sodium hydroxide in 40 ml of water. Work-up, as described above, gave 16.4 g (72% of theory) of 3-[4-(4-methylbenzyl)piperazin-1-yl]propanethiol dihydrochloride as a white crystalline solid, M.p. 273°–277° C. (dec.).

EXAMPLE 18

N-Phenyl-S-{3-[4-(4-methylbenzyl)piperazin-1-yl]propyl}thiocarbamate dihydrochloride sesquihydrate The procedure described in Example 2 was followed, using 1.4 g of phenyl isocyanate, 4.0 g of 3-[4-(4-methylbenzyl)piperazin-1-yl]propanethiol dihydrochloride, 1.2 g of triethylamine and 50 ml of methylene chloride, to give 1.1 g (20% of theory) of N-phenyl-S-{3-[4-(4-methylbenzyl)piperazin-1-yl]propyl}thiocarbamate dihydrochloride sesquihydrate as a white crystalline solid, M.p. 255°–258° C.

EXAMPLE 19

3-[4-(4-Chlorobenzyl)-2,5-dimethylpiperazin-1-yl]propanethiol dihydrochloride (a) 22.0 g g of 1-bromo-3-chloropropane were added to a mixture of 33.0 g of 4-chlorobenzyl-2,5-dimethylpiperazine, 25.0 g of potassium hydroxide and 125 ml of dimethyl sulfoxide. After stirring the solution for 3 hours at room temperature, water was added, the product was extracted with ether, and the extract was dried (magnesium sulfate) and concentrated to give 25.8 g (58% of theory) of 1-(4-chlorobenzyl)-2,5-dimethyl-4-(3-chloropropyl)piperazine as an oil, suitable for use in the next reaction.

(b) The procedure described in Example 1(b) was followed, using 12.7 g of thiourea and 26.0 g of 1-(4-chlorobenzyl)-2,5-dimethyl-4-(3-chloropropyl)piperazine in 250 ml of reagent ethanol. The hydrolysis was effected with 10.0 g of sodium hydroxide in 50 ml of water. Work-up, as described above, gave 26.5 g (83% of theory) of 3-[4-(4-chlorobenzyl)-2,5-dimethylpiperazin-1-yl]propanethiol dihydrochloride as a white crystalline solid, M.p. 168°–171° C.

EXAMPLE 20

N-Phenyl-S-{3-[4-(4-chlorobenzyl)-2,5-dimethylpiperazin-1-yl]propyl}thiocarbamate dihydrochloride The procedure described in Example 2 was followed, using 1.2 g of phenyl isocyanate, 4.0 g of 1-(4-chlorobenzyl)-2,5-dimethyl-4-(3-chloropropyl)piperazine dihydrochloride, 2.0 g of triethylamine and 50 ml of methylene chloride, to give 1.1 g (22% of theory) of N-phenyl-S-{3-[4-(4-chlorobenzyl)-2,5-dimethylpiperazin-1-yl]propyl}thiocarbamate dihydrochloride as a white crystalline solid, M.p. 215°–218° C.

EXAMPLE 21

3-[4-(1-Phenylethyl)piperazin-1-yl]propanethiol dihydrochloride (a) The procedure described in Example 17(a) was followed, using 16.5 g of 1-(1-phenylethyl)piperazine, 8.0 g of potassium hydroxide, 125 ml of dimethyl sulfoxide and 9.5 g of 1-bromo-3-chloropropane. Work-up, as described above, gave 28.0 g (96% of theory) of 1-(1-phenylethyl)-4-(3-chloropropyl)piperazine dihydrochloride as a white crystalline solid.

(b) The procedure described in Example 1(b) was followed, using 9.8 g of thiourea, 29.0 g of 1-(1-phenylethyl)-4-(3-chloropropyl)piperazine dihydrochloride, 8.3 g of triethylamine and 250 ml of reagent ethanol. The hydrolysis was effected with 6.0 g of sodium hydroxide in 40 ml of water. Work-up, as above, gave 14.5 g (51% of theory) of 3-[4-(1-phenylethyl)piperazin-1-yl]propanethiol dihydrochloride as a white crystalline solid, M.p. 252°–255° C.

EXAMPLE 22

N-Phenyl-S-{3-[4-(1-phenylethyl)piperazin-1-yl]propyl}thiocarbamate dihydrochloride dihydrate The procedure described in Example 2 was followed, using 1.6 g of phenyl isocyanate, 4.5 g of 3-[4-(1-phenylethyl)piperazin-1-yl]propanethiol dihydrochloride, 1.3 g of triethylamine and 50 ml of methylene chloride, to give 2.1 g (38% of theory) of N-phenyl-S-{3-[4-(1-phenylethyl)piperazin-1-yl]propyl}thiocarbamate dihydrochoride dihydrate as a white crystalline solid, M.p. 227°–229° C.

EXAMPLE 23

3-(4-Phenethylpiperazin-1-yl)propanethiol dihydrochloride (a) The procedure described in Example 1(a) was followed, using 29.4 g of 1-phenethyl piperazine, 25.0 g of potassium hydroxide, 100 ml of dimethyl sulfoxide and 24.0 g of 1-bromo-3-chloropropane. Work-up, as described above, gave 32.6 g (64% of theory) of 1-phenethyl-4-(3-chloropropyl)piperazine dihydrochloride as an off-white crystalline solid.

(b) The procedure described in Example 1(b) was followed, using 15.2 g of thiourea, 32.6 g of 1-phenethyl-4-(3-chloropropyl)piperazine dihydrochloride, 20.0 g of triethylamine and 250 ml of reagent ethanol The hydrolysis was effected with 10.0 g of sodium hydroxide in 40 ml of water. Work-up, as described above, gave 26.4 g (79% of theory) of 3-(4-phenethylpiperazin-1-yl)propanethiol dihydrochloride as an off-white crystalline solid, M.p. 269°–272° C.

EXAMPLE 24

N-Phenyl-S-[3-(4-phenethylpiperazin-1-yl)propyl]thiocarbamate dihydrochloride monohydrate The procedure described in Example 2 was followed, using 1.4 g of phenyl isocyanate, 4.0 g of 3-(4-phenethylpiperazin-1-yl)propanethiol dihydrochloride, 2.4 g of triethylamine and 50 ml of methylene chloride, to give 1.9 g (35% of theory) of N-phenyl-S-[3-(4-phenethylpiperazin-1-yl)propyl]thiocarbamate dihydrochloride monohydrate as a white crystalline solid, M.p. 272°–275° C.

EXAMPLE 25

3-[4-(4-Chlorophenethyl)piperazin-1-yl]propanethiol dihydrochloride (a) The procedure described in Example 17(a) was followed, using 6.5 g of 1-(4-chlorophenethyl)piperazine, 6.0 g of potassium hydroxide, 125 ml of dimethyl sulfoxide and 4.6 g of 1-bromo-3-chloropropane. Work-up, as described above, gave 6.4 g (59% of theory) of 1-(4-chlorophenethyl)-4-(3-chloropropyl)piperazine dihydrochloride as a white crystalline solid.

(b) The procedure described in Example 1(b) was followed, using 1.3 g of thiourea, 6.4 g of 1-(4-chlorophenethyl)-4-(3-chloropropyl)piperazine dihydrochloride, 1.6 g of triethylamine and 150 ml of reagent ethanol. The hydrolysis was effected with 3.5 g of sodium hydroxide and 40 ml of water. Work-up, as described above, gave 5.6 g (89% of theory) of 3-[4-(4-chlorophenethyl)piperazin-1-yl]propanethiol dihydrochloride as a white crystalline solid, M.p. 279°–281° C.

EXAMPLE 26

N-Phenyl-S-{3-[4-(4-chlorophenethyl)piperazin-1-yl]propyl}thiocarbamate dihydrochloride monohydrate The procedure described in Example 2 was followed, using 1.6 g of phenyl isocyanate, 5.0 g of 3-[4-(4-chlorophenethyl)piperazin-1-yl]propanethiol dihydrochloride, 1.3 g of triethylamine and 50 ml of methylene chloride, to give 3.0 g (44% of theory) of N-phenyl-S-{3-[4-(4-chlorophenethyl)piperazin-1-yl]propyl}thiocarbamate dihydrochloride monohydrate as a white crystalline solid, M.p. 237°–239° C.

EXAMPLE 27

N-(4-n-Butylphenyl)-S-{3-[4-(4-chlorophenethyl)piperazin-1-yl]propyl}thiocarbamate dihydrochloride The procedure described in Example 2 was followed, using 1.4 g of 4-n-butylphenyl isocyanate, 3.0 g of 3-[4-(4-chlorophenethyl)piperazin-1-yl]propanethiol dihydrochloride, 0.8 g of triethylamine and 50 ml of methylene chloride, to give 1.1 g (25% of theory) of N-(4-n-butylphenyl)-S-{3-[4-(4-chlorophenethyl)piperazin-yl]propyl}thiocarbamate dihydrochloride as a white crystalline solid, M.p. 252°–254° C.

EXAMPLE 28

N-(4-Methoxyphenyl)-S-{3-[4-(4-chlorophenethyl)piperazin-1-yl]propyl}thiocarbamate dihydrochloride The procedure described in Example 2 was followed, using 1.7 g of 4-methoxyphenyl isocyanate, 4.0 g of 3-[4-(4-chlorophenethyl)piperazin-1-yl]propanethiol dihydrochloride, 1.1 g of triethylamine and 50 ml of methylene chloride, to give 1.4 g (25% of theory) of N-(4-methoxyphenyl)-S-{3-[4-(4-chlorophenethyl)piperazin-1-yl]propyl}thiocarbamate dihydrochloride as a white crystalline solid, M.p. 236°–238° C.

EXAMPLE 29

N-(3,4,5-Trimethoxyphenyl)-S-{3-[4-(4-chlorophenethyl)piperazin-1-yl]propyl}thiocarbamate dihydrochloride The procedure described in Example 2 was followed, 2.5 g of 3,4,5-trimethoxyphenyl isocyanate, 4.4 g of 3-[4-(4-chlorophenethyl)piperazin-1-yl]propanethiol dihydrochloride, 1.2 g of triethylamine and 50 ml of methylene chloride, to give 1.6 g (23% of theory) of N-(3,4,5-trimethoxyphenyl)-S-{3-[4-(4-chlorophenethyl)piperazin-1-yl]propyl}thiocarbamate dihydrochloride as a white crystalline solid, M.p. 239°–241° C.

EXAMPLE 30

3-[4-(3-Phenylpropyl)piperazin-1-yl]propanethiol dihydrochloride (a) The procedure described in Example 17(a) was followed, using 36.0 g of (3-phenylpropyl)piperazine, 25.0 g of potassium hydroxide, 125 ml of dimethyl sulfoxide and 28.0 g of 1-bromo-3-chloropropane, to give 46.0 g (73% of theory) of 1-(3-phenylpropyl)-4-(3-chloropropyl)piperazine dihydrochloride.

(b) The procedure described in Example 1(b) was followed, using 19.0 g of thiourea, 44.0 g of 1-(3-phenylpropyl)-4-(3-chloropropyl)piperazine dihydrochloride, 25 g of triethylamine and 250 ml of reagent ethanol. The hydrolysis was effected with 10.0 g of sodium hydroxide in 50 ml of water. Work-up, as described above, gave 35.8 g (82% of theory) of 3-[4-(3-phenylpropyl)-piperazin-1-yl]propanethiol dihydrochloride as a white crystalline solid, M.p. 237°–239° C.

EXAMPLE 31

N-Phenyl-S-{3-[4-(3-phenylpropyl)piperazin-1-yl]propyl}thiocarbamate dihydrochloride monohydrate The procedure described in Example 2 was followed, using 1.2 g of phenyl isocyanate, 4.0 g of 3-[4-(3-phenylpropyl)piperazin-1-yl]propanethiol dihydrochloride, 2.2 g of triethylamine and 50 ml of methylene chloride, to give 2.1 g (41% of theory) of N-phenyl-S-{3-[4-(3-phenylpropyl)piperazin-1-yl]propyl}thiocarbamate dihydrochloride monohydrate as a white crystalline solid, M.p. 240°–243° C.

EXAMPLE 32

3-{4-[3-(4-Chlorophenyl)propyl]piperazin-1-yl}propanethiol dihydrochloride (a) The procedure described in Example 17(a) was followed, using 27.0 g of 3-(4-chlorophenyl)propyl piperazine, 22.0 g of potassium hydroxide, 250 ml of dimethyl sulfoxide and 17.7 g of 1-bromo-3-chloropropane to give 22.9 g (54% of theory) of 1-[3-(4-chlorophenyl)propyl]-4-(3-chloropropyl)piperazine dihydrochloride.

(b) The procedure described in Example 1(b) was followed, using 7.6 g of thiourea, 22.9 g of 1-[3-(4-chlorophenyl)propyl]-4-(3-chloropropyl)piperazine dihydro- chloride, 5.8 g of triethylamine and 250 ml of reagent ethanol. The hydrolysis was effected with 10.0 g of sodium hydroxide in 50 ml of water. Work-up, as described above, gave 14.1 g (65% of theory) of 3-{4-[3-(4-chlorophenyl)propyl]piperazin-1-yl}propanethiol dihydrochloride as a white crystalline solid, M.p. 238°–242° C.

EXAMPLE 33

N-(4-n-Butylphenyl)-S-{3-[4-[3-(4-chlorophenyl)propyl]piperazin-1-yl]propyl}thiocarbamate dihydrochloride The procedure described in Example 2 was followed, using 2.5 g of 4-n-butylphenyl isocyanate, 5.0 g of 3-{4-[3-(4-chlorophenyl)propyl]piperazin-1-yl}propanethiol dihydrochloride, 1.4 g of triethylamine and 50 ml of methylene chloride, to give 2.7 g (34% of theory) of N-(4-n-butylphenyl-S-{3-[4-[3-(4-chlorophenyl)propyl]piperazin-1-yl]propyl}thiocarbamate dihydrochloride as a white crystalline solid, m.p. 270°–272° C.

EXAMPLE 34

3-[4-(4-Fluorophenyl)piperazin-1-yl]propanethiol dihydrochloride (a) The procedure described in Example 1(a) was followed, using 32.8 g of 1-(4-fluorobenzyl)piperazine, 30.0 g of potassium hydroxide, 100 ml of dimethyl sulfoxide and 27.0 g of 1-bromo-3-chloropropane. Work-up, as described above, gave 35.2 g (61% of theory) of 1-(4-fluorobenzyl)-4-(3-chloropropyl) piperazine dihydrochloride as a white crystalline solid.

(b) The procedure described in Example 1(b) was followed, using 15.2 g of thiourea, 35.2 g of 1-(4-fluorobenzyl)-4-(3-chloropropyl)piperazine dihydrochloride, 20.0 g of triethylamine and 200 ml of reagent ethanol. The hydrolysis was effected with 10.0 g of sodium hydroxide and 50 ml of water. Work-up, as described above, gave 15.5 g (58% of theory) of 3-[4-(4-fluorophenyl)piperazin-1-yl]propanethiol. The salt was precipitated with ethereal hydrochloric acid to give 3-[4-(4-fluorophenyl)piperazin-1-yl]propanethiol dihydrochloride as a white crystalline solid, M.p. 284°–287° C. (dec.).

EXAMPLE 35

N-Phenyl-S-{3-[4-(4-fluorophenyl)piperazin-1-yl]propyl}thiocarbamate dihydrochloride 1.2 g of phenyl isocyanate was added to a solution of 2.5 g of 3-[4-(4-fluorophenyl)piperazin-1-yl]propanethiol in 75 ml of methylene chloride, and the mixture was refluxed for four hours. After the further addition of 100 ml of methylene chloride the solution was washed with water, dried (sodium sulfate) and concentrated. The salt was precipitated with ethereal hydrochloric acid and recrystallized from aqueous ethanol to give 1.35 g (33% of theory) of N-phenyl-S-{3-[4-(4-fluorophenyl)piperazin-1-yl]propyl}thiocarbamate dihydrochloride as a white crystalline solid, M.p. 250°–252° C.

EXAMPLE 36

2-[4-(4-Chlorobenzyl)piperazin-1-yl]ethanethiol dihydrochloride (a) A mixture of 15.0 g of 1-(4-chlorobenzyl)piperazine, 14.4 g of 1-bromo-2-chloroethane and 150 ml of tetrahydrofuran was refluxed for 8 hours. The solvent was removed in vacuo, and 2N sodium hydroxide was added to the residue. The product was extracted with methylene chloride, and the extract was dried (sodium sulfate) and concentrated. The salt was precipitated with ethereal hydrochloric acid to give 13.8 g (56% of theory) of 1-(4-chlorobenzyl)-4-(2-chloroethyl)piperazine dihydrochloride as a white crystalline solid.

(b) The procedure described in Example 1(b) was followed, using 6.1 g of thiourea, 13.8 g of 1-(4-chlorobenzyl)-4-(2-chloroethyl)piperazine dihydrochloride, 4.1 g of triethylamine and 150 ml of reagent ethanol. The hydrolysis was effected with 7.0 g of sodium hydroxide and 50 ml of water. Work-up, as described above, gave 6.7 g (62% of theory) of 2-[4-(4-chlorobenzyl)piperazin-1-yl]ethanethiol dihydrochloride as a white crystalline solid, M.p. 244°–247° C.

EXAMPLE 37

N-phenyl-S-{2-[4-(4-chlorobenzyl)piperazin-1-yl]ethyl} thiocarbamate dihydrochloride The procedure described in Example 35 was followed, using 1.3 g of phenyl isocyanate, 3.0 g of 2-[4-(4-chlorobenzyl)piperazin-1-yl]ethanethiol and 100 ml of methylene chloride, to give 2.2 g (43% of theory) of N-phenyl-S-{2-[4-(4-chlorobenzyl)piperazin-1-yl]ethyl} thiocarbamate dihydrochloride as a white crystalline solid, M.p. 232°–236° C. (dec.).

EXAMPLE 38

N Cyclohexyl-S-{3-[4-(4-chlorophenethyl)piperazin-1-yl]propyl}thiocarbamate dihydrochloride The procedure described in Example 35 was followed, using 1.7 g of cyclohexyl isocyanate, 4.0 g of 3-[4-(4-chlorophenethyl)piperazin-1-yl]propanethiol and 100 ml of methylene chloride, to give 3.8 g (58% of theory) of N-cyclohexyl-S-{3-[4-(4-chlorophenethyl)piperazin-1-yl]propyl}thiocarbamate dihydrochloride as a white crystalline solid, M.p. 262°–267° C.

EXAMPLE 39

N-(4-Methoxyphenyl)-S-{3-[4-[3-(4-chlorophenyl)propyl]piperazin-1-yl]propyl]thiocarbamate dihydrochloride hemihydrate The procedure described in Example 35 was followed, using 2.0 g of 4-methoxyphenyl isocyante, 4.0 g of 3-{4-[3-(4-chlorophenyl)propyl]piperazin-1-yl}propanethiol and 100 ml of methylene chlorine to give 3.4 g (48% of theory) of N-(4-methoxyphenyl)-S-{3-[4-[3-(4-chlorophenyl)propyl]piperazin-1-yl]propyl} thiocarbamate dihydrochloride hemihydrate as a white crystalline solid, M.p. 240°–244° C.

EXAMPLE 40

N-(n-Hexyl)-S-{3-[4-(4-chlorobenzyl)piperazin-1-yl]propyl}thiocarbamate dihydrochloride The procedure described in Example 35 was followed, using 1.4 g of n-hexyl isocyanate, 3.0 g of 3-[4-(4-chlorobenzyl)piperazin-1-yl]propanethiol and 100 ml of methylene chloride, to give 2.7 g (51% of theory) of N-(n-hexyl)-S-{3-[4-(4-chlorobenzyl)piperazin-1-yl]propyl}thiocarbamate dihydrochloride as a white crystalline solid, M.p. 249°–252° C. (dec.).

EXAMPLE 41

3-{4-[4-(4-Chlorophenyl)butyl]piperazin-1-yl}propanethiol dihydrochloride (a) The procedure described in Example 1(a) was followed, using 10.0 g of 4-(4-chlorophenyl)butyl piperazine, 47.2 g of 1-bromo-3-chloropropane, 150 ml of dimethyl sulfoxide and 11.2 g of potassium hydroxide, to give 10.0 g (82% of theory) of 1-[4-(4-chlorophenyl)butyl]-4-(3-chloropropyl)piperazine dihydrochloride as a white crystalline solid, M.p. 266°–268° C.

(b) The procedure described in Example 1(b) was followed, using 1.0 g of thiourea, 4.0 g of 1-[4-(4-chlorophenyl)butyl]-4-(3-chloropropyl)piperazine dihydrochloride and 50 ml of reagent ethanol. The hydrolysis was effected with 4.0 g of sodium hydroxide in 50 ml of water. Work-up of the free base, as described above, followed by purification on a silica gel column (methylene chloride:methanol, 97:3), precipitation as the hydrochloride salt and recrystallization from reagent ethanol, gave 0.6 g (16% of theory) of 3-{4-[4-(4-chlorophenyl)butyl]piperazin-1-yl}propanethiol dihydrochloride as a white crystalline solid, M.p. 254°–259° C.

EXAMPLE 42

N-(n-Hexyl)-S-{3-[4-[4-(4-chlorophenyl)butyl]piperazin-1-yl]propyl}thiocarbamate dihydrochloride The procedure described in Example 2 was followed, using 1.0 g of n-hexyl isocyanate, 2.6 g of 3-{4-[4-(4-chlorophenyl)butyl]piperazin-1-yl}propanethiol and 25 ml of methylene chloride, to give 1.4 g (32% of theory) of N-(n-hexyl)-S-{3-[4-[4-(4-chlorophenyl)butyl]piperazin-1-yl]propyl}thiocarbamate dihydrochloride as a white crystalline solid, M.p. 235°–245° C. (dec.).

EXAMPLE 43

3-(4-Cinnamylpiperazin-1-yl)propanethiol dihydrochloride (a) 6.0 g of cinnamyl bromide were added to a mixture of 7.4 g of 1-(3-chloropropyl)piperazine dihydrochloride hemihydrate, 6.1 g of triethylamine and 100 ml of reagent ethanol. The mixture was refluxed for 4 hours and then stirred overnight. After removal of the solvent in vacuo, water was added to the residue. The product was then extracted with ether and the extract was dried (magnesium sulfate) and concentrated. The resulting oil was chromatographed on silica gel (methylene chloride/methanol: 9/1) and precipitated with ethereal hydrochloric acid to give 7.4 g (70% of theory) of 1-cinnamyl-4-(3-chloropropyl)piperazine dihydrochloride.

(b) The procedure described in Example 1(b) was followed, using 3.1 g of thiourea, 7.4 g of 1-cinnamyl-4-(3-chloropropyl)piperazine dihydrochloride, 4,1 g of triethylamine and 100 ml of reagent ethanol. The hydrolysis was effected with 3.0 g of sodium hydroxide in 30 ml of water. Work-up, as described above, gave 3.6 g (52% of theory) of 3-(4-cinnamylpiperazin-1-yl)propanethiol dihydrochloride as a white crystalline solid, M.p. 249°–252° C.

EXAMPLE 44

N-(n-Hexyl)-S-[3-(4-cinnamylpiperazin-1-yl)propyl]thiocarbamate dihydrochloride

The procedure described in Example 2 was followed, using 0.4 g of n-hexyl isocyanate, 1.0 g of 3-(4-cinnamylpiperazin-1-yl)propanethiol dihydrochloride, 0.6 g of triethylamine and 50 ml of methylene chloride, to give 0.44 g (31% of theory) of N-(n-hexyl)-S-[3-(4-cinnamylpiperazin-1-yl)propyl]thiocarbamate dihydrochloride as a white crystalline solid, M.p. 251°–253° C.

EXAMPLE 45

3-[4-(4-Chlorobenzyl)homopiperazin-1-yl]propanethiol (a) 15.7 g of 1-bromo-3-chloropropane were added to a cooled solution of 15.0 g of 1-(4-chlorobenzyl)-homopiperazine and 12.0 g of potassium hydroxide in 50 ml of dimethyl sulfoxide. The mixture was stirred at 5°-10° C. for one hour, and then an additional 30 minutes at room temperature. After the addition of ice water, the product was extracted with ether, and the extract was dried (magnesium sulfate) and concentrated in vacuo. Final purification was effected on a silica gel column (methylene chloride:methanol, 9:1), and the solvent was removed in vacuo to give 8.4 g (42% of theory) of 1-(4-chlorobenzyl)-4-(3-chloropropyl)-homopiperazine as an oil.

(b) 4.1 g of thiourea were added to a mixture of 8.0 g of 1-(4-chlorobenzyl)-4-(3-chloropropyl)homopiperazine and 100 ml of reagent ethanol. The mixture was refluxed for 6 hours and then stirred overnight at room temperature. A solution of 5.0 g of sodium hydroxide in 30 ml of water was added, and the resulting solution was refluxed for 4 hours. The ethanol was removed in vacuo, and water was added to the residue. The product was extracted with methylene chloride, and the extract was dried (sodium sulfate) and concentrated to give 3.1 g (39% of theory) of 3-[4-(4-chlorobenzyl)homopiperazin-1-yl]propanethiol as a yellow oil.

EXAMPLE 46

N-(n-Hexyl)-S-{3-[4-(4-chlorobenzyl)homopiperazin-1-yl]propyl}thiocarbamate dihydrochloride The procedure described in Example 2 was followed, using 1.3 g of n-hexyl isocyanate, 3.0 g of 3-[4-(4-chlorobenzyl)homopiperazin-1-yl]propanethiol and 75 ml of methylene chloride, to give 1.3 g (33% of theory) of N-(n-hexyl)-S-{3-[4-(4-chlorobenzyl)homopiperazin-1-yl]propyl}thiocarbamate dihydrochloride as a tan powder, M.p. 183°-187° C.

EXAMPLE 47

N-(t-Butyl)-S-{3-[4-(4-chlorobenzyl)piperazin-1-yl]propyl}thiocarbamate dihydrochloride sesquihydrate The procedure described in Example 2 was followed, using 0.8 g of t-butyl isocyanate, 3.0 g of 3-[4-(4-chlorobenzyl)piperazin-1-yl]propanethiol dihydrochloride, 1.6 g of triethylamine and 75 ml of methylene chloride, to give 2.2 g (60% of theory) of N-(t-butyl)-S-{3-[4-(4-chlorobenzyl)piperazin-1-yl]propyl}thiocarbamate dihydrochloride sesquihydrate as a white crystalline solid, M.p. 246°-248° C.

EXAMPLE 48

The in vitro inhibition of histamine release from human leukocytes (basophils), from rat peritoneal mast cells and from guinea pig basophils by the compounds of formula I can be demonstrated according to the following biochemical test procedures:

A. Procedure for Determining Inhibition of Histamine Release from Human Leukocytes (Basophils)

1. Separation of Leukocytes: A modification of the method of L. Lichtenstein and A. Osler, *J. Exp. Med.* 120, 507 (1964) is used. Heparinized human blood (80-100 ml) is mixed with 20 ml of saline (0.2%) containing 0.6 gm of dextrose and 1.2 gm of dextran in propylene centrifuge tubes. The mixture is kept at ambient temperature for 60-90 minutes to allow the separation of erythrocytes from the platelet-leukocyte-rich supernate. The supernate is removed and centrifuged for 8 minutes at 110 $\times$g in cold. The leukocyte pellet is washed twice with Tris buffer and finally suspended in 150-180 ml Tris-ACM buffer at 1-2 $\times 10^6$ cells/ml.

2. Reaction Mixture: The reaction is carried out in 12$\times$75 mm plastic tubes at a total volume of 1.23 ml. The reaction medium includes 0.05 ml rabbit anti-human IgE (the antigen), 0.2 ml of the test compound in water at concentrations ranging from 10-100 $\mu$M, and 1.0 ml of the leukocyte suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of W. Siraganian and W. Hook in Chapter 102 of the *Manual of Clinical Immunology*, 2nd Edition, edited by R. Rose and H. Friedman, published by the American Society for Microbiology, Washington, D.C., 1980. Percent inhibition is calculated as follows:

$$\frac{(\text{Control} - \text{blank}) - (\text{Test sample} - \text{blank})}{(\text{Control} - \text{blank})} \times 100$$

The concentration which causes a 50 percent inhibition (IC$_{50}$) of histamine release is interpolated from a plot of percent inhibition versus logarithm of drug concentration.

B. Procedure for Determining Inhibition of Histamine Release from Rat Peritoneal Mast Cells 1. Harvest of Peritoneal Mast Cells: After the rats are sacrificed with ether, 20 ml of Minimum Essential Medium (MEM) containing 20 units/ml heparin is injected into the peritoneum. The abdomen is massaged for one minute and the lavage fluid collected. The peritoneal cells are centrifuged at 1800 rpm for 8 minutes in cold. After two washes with Tris A buffer, the cells are resuspended in Tris ACM buffer at 2-4$\times 10^6$ cells/ml.

2. Reaction mixture: The reaction is carried out in 12$\times$75 mm plastic tubes at a total volume of 1.25 ml. The reaction mixture includes 0.5 ml (10-1000 $\mu$g) sheep anti-rat IgE or ovalbumin, 0.2 ml of the test compound in water at concentrations ranging from 10-1000 $\mu$M, 0.5 ml phosphatidylserine solution (20-60 $\mu$g to each tube), and 0.5 ml of cell suspension.

The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of Siraganian, supra.

The concentration which causes a 50% inhibition (IC$_{50}$) of histamine release is computed as in Part A.

C. Procedure for Determining Inhibition of Histamine Release from Guinea Pig Basophils 1. In Vivo Sensitization: Male Hartley guinea pigs (200-300 gm) are immunized on day 0 with two 0.05 ml intradermal injections of 200 $\mu$g ovalbumin. Sensitized basophils are available between days 13–25 post-sensitization. This mode of sensitization favors IgE response.

2. Separation of Leukocytes: The method of Lett-Brown et al., *Int. Arch. Allergy, Appl. Immun.* 64, 241 (1981) is used. Animals are anesthetized with ether and are bled via cardiac puncture, with plastic syringes containing sufficient EDTA to provide a final concentration of 10 mM.

One part of 3% gelatin in saline at 37° C. is mixed with 2 parts of blood in a 16×150 mm tube. The cells are allowed to sediment at a 30° angle for 45 minutes in a 37° C. water bath. The leukocyte-rich plasma is collected and centrifuged at 150×g for 30 minutes at room temperature. The pelleted cells are washed in Hepes-buffered saline (HG) containing 4 mM EDTA and resuspended in Hepes-buffered saline containing $Mg^{1+}$ and $Ca^{++}$ (HGCM) at 4–5×10$^6$ cells/ml.

3. Reaction Mixture: The reaction is carried out in 12×75 mm plastic tubes and a total volume of 1.2 ml which includes 0.5 ml of antigen, 0.2 ml of drug solution at concentrations ranging from 10–1000 μM and 0.5 ml of prewashed cell suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

4. Histamine Assay: Histamine release is measured by the automated fluorometric method of Siraganian, supra. The concentration which causes a 50 percent inhibition of histamine release is computed as in Part A.

The results of the testing of compounds of formula I for the inhibition of histamine release from human leukocytes (basophils) according to Procedure A, from rat peritoneal mast cells according to Procedure B, and from guinea pig basophils according to Procedure C, are shown in Table 1 below:

TABLE 1

| Test Compound (Example No.) | In Vitro Inhibition of Histamine Release IC$_{50}$ (μM) | | |
|---|---|---|---|
| | Procedure A[a] | Procedure B[b] | Procedure C[c] |
| 1 | 140 | NS | NS |
| 2 | 310 | NS | NS |
| 3 | 4 | NS | NS |
| 4 | Int. | NS | NS |
| 5 | Int. | NS | NS |
| 6 | 5 | 3 | 20 |
| 7 | 2.6 | 3 | 13 |
| 8 | 760 | NS | NS |
| 9 | 11 | NS | NS |
| 10 | 47 | NS | NS |
| 11 | >1000[d] | NS | NS |
| 12 | >300[d] | NS | NS |
| 13 | 140 | NS | NS |
| 14 | 100 | NS | NS |
| 15 | 100 | NS | NS |
| 16 | >100[d] | NS | NS |
| 17 | 24 | NS | NS |
| 18 | >1000[d] | NS | NS |
| 19 | NS | NS | NS |
| 20 | >1000[d] | NS | NS |
| 21 | NS | NS | NS |
| 22 | 67 | NS | NS |
| 23 | NS | NS | NS |
| 24 | >1000[d] | NS | NS |
| 25 | 5 | 4 | 5 |
| 26 | 25 | NS | NS |
| 27 | 30 | NS | NS |
| 28 | 5 | 7 | 40 |
| 29 | 9 | NS | NS |
| 30 | NS | NS | NS |
| 31 | >100[d] | NS | NS |

TABLE 1-continued

| Test Compound (Example No.) | In Vitro Inhibition of Histamine Release IC$_{50}$ (μM) | | |
|---|---|---|---|
| | Procedure A[a] | Procedure B[b] | Procedure C[c] |
| 32 | NS | NS | NS |
| 33 | 5 | 2 | 14 |
| 34 | NS | NS | NS |
| 35 | >1000[d] | NS | NS |
| 36 | 3 | 5 | >100[d] |
| 37 | 3 | NS | NS |
| 38 | 10 | NS | NS |
| 39 | 13 | NS | NS |
| 40 | 71 | NS | NS |
| 41 | NS | NS | NS |
| 42 | >10[d] | NS | NS |
| 43 | NS | NS | NS |
| 44 | >1000[d] | NS | NS |
| 45 | 3 | NS | NS |
| 46 | 12 | NS | NS |
| 47 | 58 | NS | NS |

Int. = Compound interferes with test.
NS = Not submitted for testing.
[a]From human basophils.
[b]From rat peritoneal mast cells.
[c]From guinea pig basophils.
[d]No response detected at highest dose indicated.

EXAMPLE 49

The antagonism of the effects of histamine on the contraction of isolated guinea pig ileum by the compounds of formula I can be determined by the procedure of G. Possanza, A. Bauen, and P. Stewart, *Int. Arch. Allergy Appl. Immunol.*, 49, 289 (1975). The degree of inhibition is determined as the difference between the contraction caused by histamine (final concentration 0.2 μg/ml) alone and that seen in the presence of both histamine and the test compound. The inhibitory activity of the test compound is expressed as that concentration of the compound which causes a 50% reduction of the contractile response (IC$_{50}$).

When tested according to the above procedure, compounds of formula I gave the results shown in TABLE 2 below:

TABLE 2

| Test Compound (Example No.) | Inhibition IC$_{50}$ (μM) |
|---|---|
| 4 | 0.19 |
| 5 | 0.21; 0.30 |
| 6 | 0.06 |
| 9 | 0.12 |
| 14 | 0.12 |
| 26 | 0.06 |
| 28 | 0.12; 0.09 |
| 29 | 0.18 |

EXAMPLE 50

Topical solution (ophthalmic or nasal)

The solution composition is compounded from the following ingredients:

| | |
|---|---|
| 2-[4-(4-chlorobenzyl)piperazin-1-yl]-ethanethiol dihydrochloride | 0.100 g |
| Disodium hydrogen phosphate.7 H$_2$O | 1.073 g |
| Dihydrogen sodium phosphate.H$_2$O | 0.386 g |
| Sodium chloride | 0.387 g |
| Distilled water q.s. ad | 100 ml |

The ingredients are dissolved in the conventional manner to form an aqueous solution. The solution is appropriately filtered, with the ophthalmic solution requiring sterile filtration. Each ml of the solution contains 1.0 mg of the active ingredient.

EXAMPLE 51

Ointment

The ointment composition utilizes the following base compounded in a conventional manner.

| White petrolatum | 75 g |
|---|---|
| Mineral oil | 25 g |
| White wax | 2 g |

The active ingredient, for example 2-[4-(4-chlorobenzyl)piperazin-1-yl]ethanethiol dihydrochloride, is uniformly incorporated into the base at the required concentration, for example, 1 g of the active ingredient can be incorporated into 100 g of base.

EXAMPLE 52

Inhalation aerosol

The aerosol composition is prepared from the following ingredients:

| 2-[4-(4-chlorobenzyl)piperazin-1-yl]-ethanethiol dihydrochloride | 1.00 parts |
|---|---|
| Soybean lecithin | 0.20 parts |
| Propellant gas mixture (Freon 11, 12 and 14) q.s. ad | 100.00 parts |

The ingredients are compounded in conventional manner, and the composition is filled into aerosol containers with a metering valve which releases 0.5 to 2.0 mg of active ingredient per actuation of the valve.

Any one of the other compounds embraced by formula I or a non-toxic, pharmacologically acceptable acid addition salt thereof may be substituted for the particular active ingredient in Examples 50 through 52. Likewise, the amount of active ingredient in these illustrative examples may be varied to achieve the desired dosage unit range, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit or the scope of the appended claims.

We claim:

1. A compound of the formula

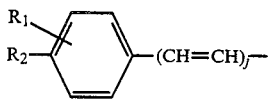

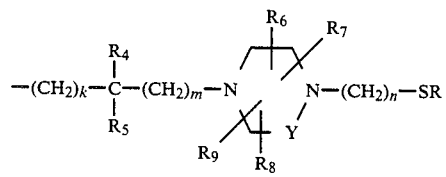

wherein

R is hydrogen or

A is alkyl of 1 to 8 carbon atoms; cycloalkyl of 3 to 7 carbon atoms; phenyl; phenyl mono- or di-substituted independently with alkyl of 1 to 4 carbon atoms, halogen, trihalomethyl, alkoxy or 1 to 3 carbon atoms, carboxylic acyl or 1 to 3 carbon atoms, carboxyl, (alkoxy of 1 to 3 carbon atoms) carbonyl, nitro, cyano or di(alkyl of 1 to 3 carbon atoms)amino; or phenyl tri-substituted with alkoxy of 1 to 3 carbon atoms;

$R_1$ and $R_2$ are independently hydrogen, halogen, alkyl of 1 to 4 carbon atoms, trihalocmethyl, nitro, cyano, di(alkyl of 1 to 4 carbon atoms)- amino, (alkoxy of 1 to 4 carbon atoms)carbonyl, alkoxy of 1 to 4 carbon atoms or hydroxyl;

$R_4$ and $R_5$ are indenpendently hydrogen; alkyl of 1 to 4 carbon atoms, or phenyl;

$R_6$, $R_7$, $R_8$ and $R_9$ are independently hydrogen or methyl;

Y is $-CH_2-$;

j is 0 or 1;

k and m are independently 0, 1, 2, or 3, their sum being no more than 6 and must be 0 when j is 1;

n is 2, 3, or 4, with the proviso that n must be 3 or 4 when $R_1$ is hydrogen or 2-methyl, $R_2$, $R_4$, $R_5$, $R_6$, $R_7$, $R_8$, $R_9$ and R are ach hydrogen and j, k, and m are each 0, and Y is $-CH_2-$;

or a non-toxic, pharmaceutically acceptable acid addition salt thereof.

2. A compound as defined in claim 1 wherein R is hydrogen.

3. A compound as defined in claim 2 of the formula

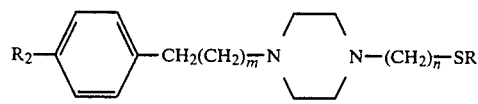

wherein

R is hydrogen or

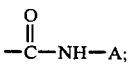

A is alkyl of 1 to 8 carbon atoms; cycloalkyl of 3 to 7 carbon atoms; phenyl; phenyl mono- or di-substituted, independently with alkyl of 1 to 4 carbon atoms, halogen, trihalomethyl, alkoxy of 1 to 3 carbon atoms, carboxylic acyl of 1 to 3 carbon atoms, carboxyl, (alkoxy of 1 to 3 carbon atoms)-carbonyl, nitro, cyano or di(alkyl of 1 to 3 carbon atoms)amino; or phenyl tri-substituted with alkoxy of 1 to 3 carbon atoms;

$R_2$ is hydrogen, halogen, alkyl of 1 to 4 carbon atoms, trihalomethyl, nitro, cyano, di(alkyl of 1 to 4 carbon atoms)amino, (alkoxy of 1 to 4 carbon atoms)-carbonyl, alkoxyl of 1 to 4 carbon atoms or hydroxyl;

m is 0, 1, 2, or 3, their sum being no more than 6 and must be 0 when j is 1; and n is 2 or 3, with the proviso than n must be 3, when R₂ is hydrogen or 2-methyl, R is hydrogen, and m is 0.

4. A compound as defined in claim 3 wherein R is hydrogen.

5. A compound as defined in claim 3 wherein R is —CONHA wherein A is alkyl of 1 to 8 carbon atoms or cycloalkyl of 3 to 7 carbon atoms.

6. A compound as defined in claim 3 wherein R is —CONHA wherein A is phenyl.

7. A compound as defined in claim 3, 4, 5, or 6 wherein R₂ is chlorine.

8. The compound of claim 1 which is 3-[4-(4-chlorobenzyl)piperazin-1-yl]propanethiol.

9. The compound of claim 1 which is N-cyclohexyl-S-{3-[4-(4-chlorobenzyl)piperazin-1-yl]propyl}thiocarbamate.

10. The compound of claim 1 which is N-phenyl-S-{3-[4-(4-chlorobenzyl)piperazin-1-yl]propyl}thiocarbamate.

11. The compound of claim 1 which is N-(4-fluorophenyl)-S-{3-[4-(4-chlorobenzyl)piperazin-1-yl]propyl}thiocarbamate.

12. The compound of claim 1 which is 3-[4-(4-methylbenzyl)piperazin-1-yl]propanethiol.

13. The compound of claim 1 which is 3-[4-(4-chlorophenethyl)piperazin-1-yl]propanethiol.

14. The compound of claim 1 which is N-phenyl-S-{3-[4-(4-chlorophenethyl)piperazin-1-yl]propyl}thiocarbamate.

15. The compound of claim 1 which is N-(4-n-butylphenyl)-S-{3-[4-(4-chlorophenethyl)piperazin-1-yl]propyl}thiocarbamate.

16. The compound of claim 1 which is N-(4-methoxyphenyl)-S-{3-[4-(4-chlorophenethyl)piperazin-1-yl]propyl}thiocarbamate.

17. The compound of claim 1 which is N-(3,4,5-trimethoxyphenyl)-S-{3-[4-(4-chlorophenethyl)piperazin-1-yl]propyl}thiocarbamate.

18. The compound of claim 1 which is 3-{4-[3-(4-chlorophenyl)propyl]piperazin-1-yl}propanethiol.

19. The compound of claim 1 which is N-(4-n-butylphenyl)-S-{3-[4-[3-(4-chlorophenyl)propyl]piperazin-1-yl]propyl}thiocarbamate.

20. The compound of claim 1 which is 2-[4-(4-chlorobenzyl)piperazin-1-yl]ethanethiol.

21. The compound of claim 1 which is N-(phenyl-S-{2-[4-(4-chlorobenzyl)piperazin-1-yl]ethyl}thiocarbamate.

22. The compound of claim 1 which is N-cyclohexyl-S-{3-[4-(4-chlorophenethyl)piperazin-1-yl]propyl}thiocarbamate.

23. The compound of claim 1 which is N-(4-methoxyphenyl)-S-{3-[4-[3-(4-chlorophenyl)propyl]piperazin-1-yl]propyl}thiocarbamate.

24. The compound of claim 1 which is 3-{4-[4-(4-chlorophenyl)butyl]piperazin-1-yl}propanethiol.

25. The compound of claim 1 which is N-(n-hexyl)-S-{3-[4-(4-chlorobenzyl)homopiperazin-1-yl]propyl}thiocarbamate.

26. A topical antiallergic or anti-inflammatory composition consisting essentially of an inert pharmaceutical carrier and an effective antiallergic or anti-inflammatory amount of a compound of claim 1.

27. The method of suppressing allergic reactions or inflammation in a warm-blooded animal in need thereof, which comprises topically administering to said animal an effective antiallergic or anti-inflammatory amount of a compound of claim 1.

* * * * *